US00PP32037P2

(12) United States Plant Patent
Van Swieten

(10) Patent No.: US PP32,037 P2
(45) Date of Patent: Aug. 4, 2020

(54) PHALAENOPSIS ORCHID PLANT NAMED 'PHALFEPXO'

(50) Latin Name: ***Phalaenopsis* hybrid**
Varietal Denomination: PHALFEPXO

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/602,560

(22) Filed: Oct. 30, 2019

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
See application file for complete search history.

*Primary Examiner* — Susan McCormick Ewoldt
(74) *Attorney, Agent, or Firm* — Jondle & Associates, P.C.

(57) ABSTRACT

A new and distinct variety of *Phalaenopsis* plant named 'PHALFEPXO', particularly characterized by having yellow dotted flowers with small white centers and yellow-white lips, 1 to 3 peduncles that are medium long and moderate, leaves that are oblong, and is propagated by meristem tissue culture, is disclosed.

3 Drawing Sheets

Genus and species: *Phalaenopsis* hybrid.
Variety denomination: 'PHALFEPXO'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALFEPXO'.

The new *Phalaenopsis* plant is a product of a planned breeding program conducted by the inventor in Bleiswijk, the Netherlands. The objective of this breeding program was to create a new *Phalaenopsis* plant with numerous attractive yellow dotted flowers with small white centers and yellow-white lips, suitable for potted plant production.

The new *Phalaenopsis* plant 'PHALFEPXO' is a result of cross-pollination made by the inventor in April 2007 in Bleiswijk, the Netherlands, of the proprietary female, or seed parent, *Phalaenopsis* hybrid '21864-013' (unpatented) with the proprietary male, or pollen parent, *Phalaenopsis* hybrid '24245-01' (unpatented).

The new *Phalaenopsis* was selected by the inventor as a single plant within the progeny of the stated cross-pollination in a controlled greenhouse in Bleiswijk, the Netherlands, in April 2010. Asexual reproduction of the new *Phalaenopsis* plant by meristem tissue culture since 2012 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Apr. 18, 2016, by Applicant who obtained the subject matter disclosed directly from the inventor. 'PHALFEPXO' has not been made publicly available or sold anywhere in the world prior to the effective filing date of this application with the exception of sales or disclosures made one year or less before the effective filing date of this claimed invention by Applicant who obtained 'PHALFEPXO' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALFEPXO' as a new and distinct variety of *Phalaenopsis* plant:

1) Yellow dotted flowers with small white centers and yellow-white lips;
2) 1 to 3 peduncles;
3) Peduncle is medium long and moderate; and
4) Leaf shape is oblong.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in April 2019. Colors in the photographs may differ from the color values cited in the detailed botanical description, which accurately describe the actual colors of the new variety.

DESCRIPTION OF THE NEW VARIETY

Figure 1:
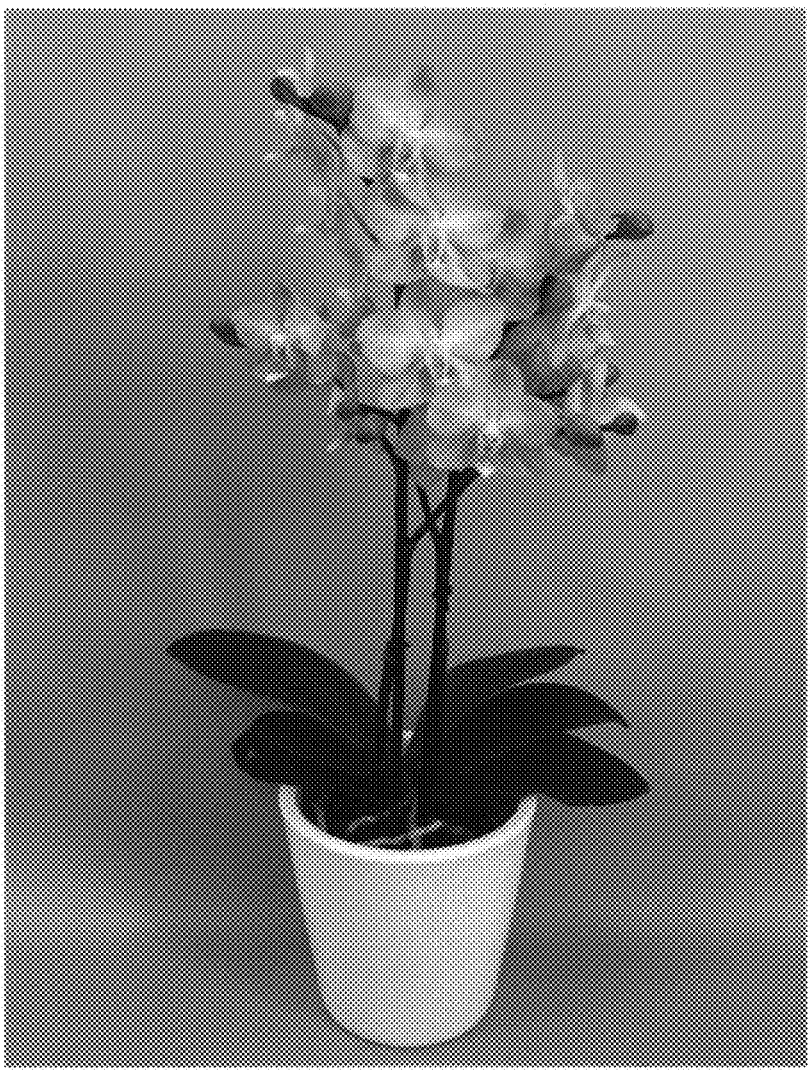
FIG. 1 shows the overall plant habit, including blooms, buds, and foliage of 'PHALFEPXO'.
Figure 2:
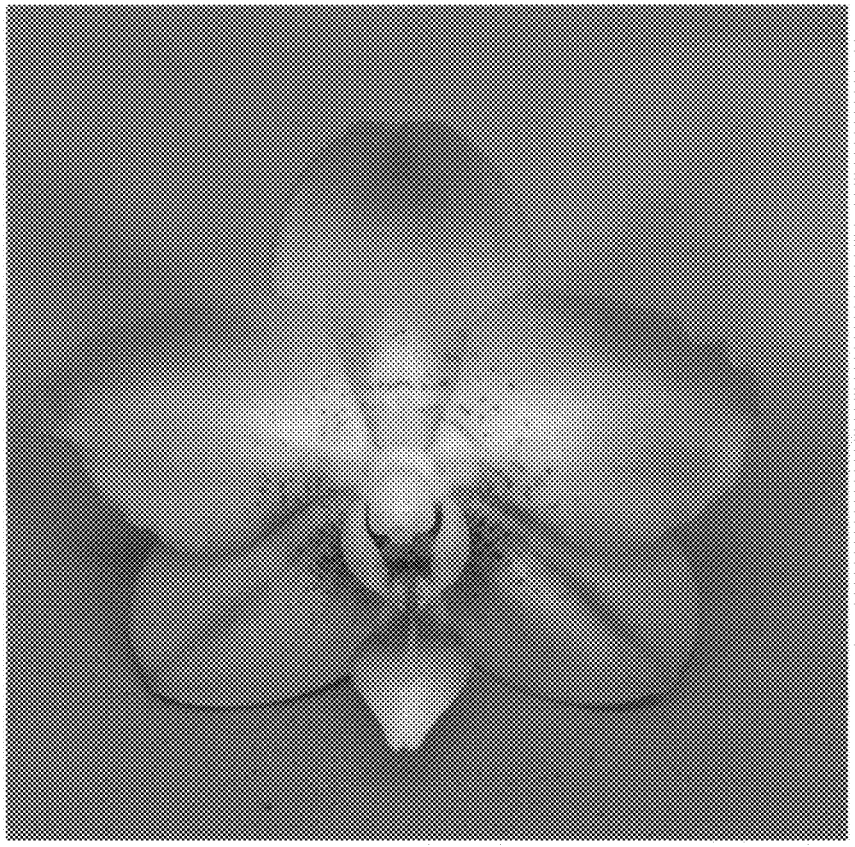
FIG. 2 shows a close-up of a flower of 'PHALFEPXO'.
Figure 3:
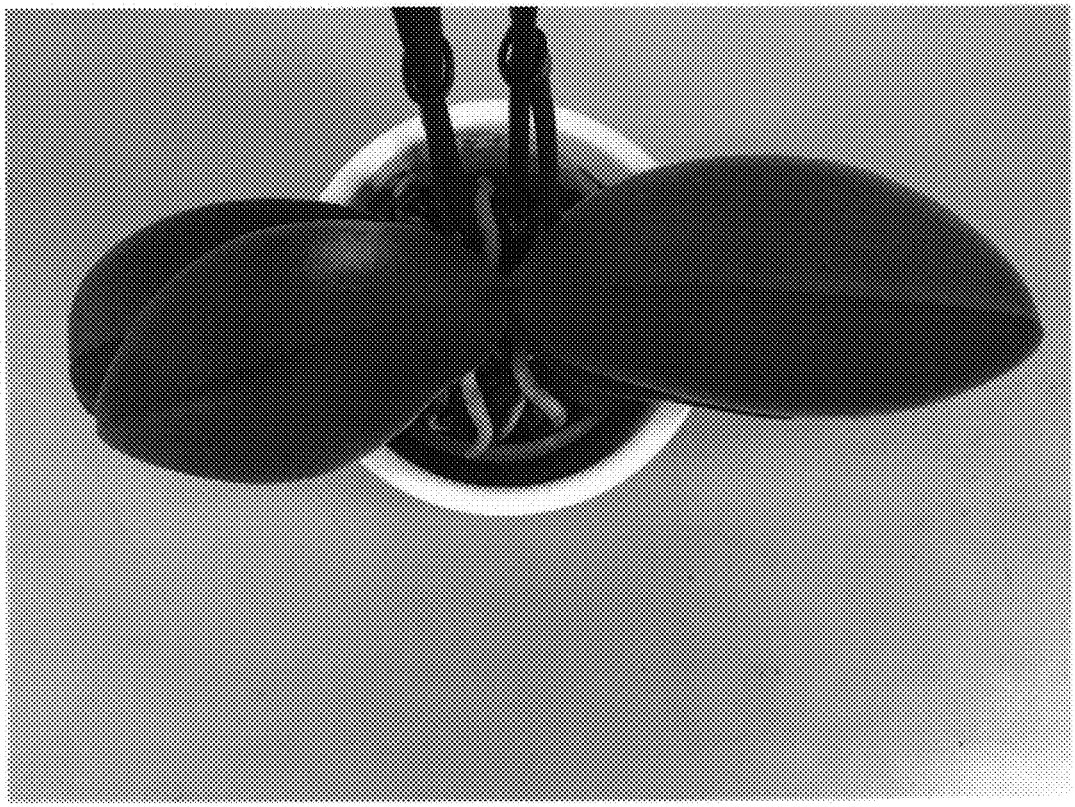
FIG. 3 shows an overhead view of the leaves of 'PHALFEPXO'.

The following detailed description sets forth the distinctive characteristics of 'PHALFEPXO'. Plants of the new

*Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in April 2019 on flowering plants which were planted in 12-centimeter (diameter) pots. After in-vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALFEPXO'.

Parentage:

*Female parent*.—*Phalaenopsis* cultivar '21864-013' (unpatented).

*Male parent*.—*Phalaenopsis* cultivar '24245-01' (unpatented).

Propagation:

*Type*.—Meristem tissue culture.

Roots:

*Root description*.—Greyed-green (between RHS 190B and 190C) colored roots with branching lateral roots having yellow-green (RHS 145A) colored root tips.

Plant:

*Commercial crop time to flowering*.—Following asexual propagation (in-vitro), the rooted cuttings grow for 20-24 weeks. After transplantation into 12-cm pots, the plants are finished after 48 to 50 weeks.

*Growth habit of peduncle*.—Upright to slightly pendant with panicle inflorescence.

*Height* (*from soil level to top of inflorescence*).—Approximately 35.0 cm to 40.0 cm.

*Width* (*measured from leaf tips*).—About 28.0 cm to 30.0 cm.

*Vigor*.—Moderate.

Leaves:

*Mature leaves*.—Quantity per plant: 6 to 8 leaves are produced before flowering. Length (fully expanded): 14.0 cm to 16.0 cm. Width: 7.5 cm to 8.5 cm. Shape: Oblong. Base shape: Moderately elongated. Apex: Obtuse unequal. Leaf blade angle with the petiole (measured from the horizontal position): Between 20 degrees and 35 degrees. Leaf margin: Ruffled at the base. Color: Upper surface: RHS 147A. Lower surface: RHS 147B. Texture (both upper and lower surfaces): Rough. Thickness: 2.0 mm to 2.5 mm. Variegation: Absent. Venation: Pattern: Parallel. Color of the midvein: Upper surface: RHS 147A. Lower surface: RHS 147B.

Peduncle:

*Quantity per plant*.—1 to 3.

*Number of flowers per peduncle*.—14 to 18.

*Length*.—35.0 cm to 40.0 cm.

*Diameter*.—5.0 mm to 6.0 mm.

*Strength*.—Strong.

*Aspect*.—Upright to slightly pendant.

*Texture*.—Smooth.

*Color*.—Mix of brown (RHS N200A) and yellow-green (RHS 144C).

*Internode length*.—5.0 cm to 6.0 cm.

Inflorescence description:

*Appearance*.—Upright to slightly pendant, panicle inflorescence with bilaterally symmetrical flowers that open in succession beginning with the lowermost flower.

*Number of inflorescences*.—1 to 3.

*Inflorescence size*.—Height (from base to tip): 210.0 mm to 250.0 mm.

*Flowering time*.—First flowers can be expected 10 to 11 months after planting in a 12-cm pot.

*Flower*.—Height: 55.0 mm to 60.0 mm. Diameter: 60.0 mm to 65.0 mm. Depth of lip: 20.0 mm to 22.0 mm.

*Flower longevity*.—On the plant: 12 to 16 weeks.

*Fragrance*.—Absent.

*Flower bud*.—Average size: Medium. Length: 16.0 mm to 18.0 mm. Width: 13.0 mm to 15.0 mm. Shape: Egg shaped. Color: Yellow-green (RHS N144C to N144D).

*Petals*.—Arrangement: Open/free. Shape: Semi-circular. Apex: Obtuse to rounded asymmetric. Margin: Undulated. Length (from base to tip): 30.0 mm to 32.0 mm. Width: 28.0 mm to 30.0 mm. Position of the broadest part of the petal: Toward the base. Color (when fully opened): Upper surface: Basic color: Yellow (RHS 7A). Over color: White (RHS NN155C) at the base; dotted (RHS 75A). Lower surface: Basic color: Greenish-yellow (RHS 7D). Over color: White (RHS NN155C) at the base with yellow edge (RHS 7B).

*Dorsal sepal*.—Shape: Elliptic. Apex: Emarginated symmetric. Margin: Entire. Length (from base to tip): 33.0 mm to 35.0 mm. Width: 26.0 mm to 28.0 mm. Color (when fully opened): Upper surface: Basic color: Yellow (RHS 7A). Over color: White (RHS NN155C) at the base; dotted (RHS 75A). and greenish-yellow (RHS 151B) toward the apex. Lower surface: Basic color: Greenish-yellow (RHS 6A). Over color: Slightly white (RHS NN155C) at the base and greenish-yellow (RHS 151C) toward the apex.

*Lateral sepals*.—Shape: Ovate. Apex: Obtuse asymmetric. Margin: Entire. Length (from base to tip): 31.0 mm to 33.0 mm. Width: .26.0 mm to 28.0 mm. Color (when fully opened): Upper surface: Basic color: Greenish-yellow (RHS 6A). Over color: Slightly white (RHS NN155C) at the base; dotted (RHS 174A). Lower surface: Basic color: Yellow-green (RHS 6B). Over color: Yellow-green midvein (RHS 151B) toward the apex.

*Labellum* (*lip*).—Whiskers: Absent. Pubescence on the lip: Absent.

*Lateral lobe*.—Shape: Type III (as described in the International Union for the Protection of New Varieties of Plants (UPOV) Test Guidelines for *Phalae-*

*nopsis*); oblong. Margin: Entire. Length: 10.0 mm to 12.0 mm. Width: 4.0 mm to 5.0 mm. Color: Light yellow (RHS 12A) at the base; dotted (RHS 173A); white (RHS NN155C) toward the tip.

*Apical lobe*.—Shape: Elliptic. Margin: Entire. Length: 16.0 mm to 18.0 mm. Width: 10.0 mm to 12.0 mm. Color: Yellow (RHS 12A) at the base with very small dots (RHS N170A); light yellow (RHS 13B) and slightly white (RHS NN155C) toward the tip. Bump and ridge: Present.

*Callus*.—Average size: Small. Height: 0.3 cm to 0.4 cm. Length: 0.2 cm to 0.3 cm. Width: 0.3 cm to 0.4 cm. Color: Yellow (RHS 7B); dotted (RHS N172B).

Reproductive organs:

*Column*.—Length: 8.0 mm to 10.0 mm. Diameter: 4.0 mm to 5.0 mm. Color: Light purple (RHS 76C) at the base and white (RHS NN155C) toward the tip.

*Pollinia*.—Quantity: 2. Diameter: 0.7 mm to 0.9 mm. Color: Orange (RHS 23A).

*Ovary*.—Length: 8.0 mm to 10.0 mm. Diameter: 2.1 mm to 2.3 mm. Color: Light yellow-green (RHS 145C) and very light yellow-green (RHS 145D) toward the flower.

*Pedicel*.—Length: 32.0 mm to 34.0 mm. Diameter: 2.4 mm to 2.7 mm. Color: Light yellow-green (RHS 145B); lighter yellow-green (RHS 145B) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALFEPXO' differs from female parent plant '21864-013' (unpatented) in that 'PHALFEPXO' has elliptic apical lobes and no whiskers, whereas '21864-013' has rhombic apical lobes and very short whiskers. Additionally, 'PHALFEPXO' has smaller flowers than '21864-013'.

'PHALFEPXO' differs from male parent plant '24245-01' (unpatented) in that 'PHALFEPXO' has elliptic apical lobes and undulated petal margins, whereas '24245-01' has rhombic apical lobes and entire petal margins.

'PHALFEPXO' is most similar to the commercial *Phalaenopsis*, plants named 'PHALCROBOH' (unpatented) and 'PHALGLAZAL' (U.S. Plant Pat. No. 29,909). 'PHALFEPXO' differs from the commercial variety 'PHALCROBOH' in that 'PHALFEPXO' has elliptic apical lobes, oblong lateral lobes, leaf margins that are ruffled at the base, and flowers with a main color of yellow (RHS 7A), whereas 'PHALCROBOH' has rhombic apical lobes, weakly spatulate lateral lobes, entire leaf margins, and flowers with a main color of yellow-green (RHS 154C). Additionally, 'PHALFEPXO' has smaller flowers than 'PHALCROBOH'.

'PHALFEPXO' differs from the commercial variety 'PHALGLAZAL' in that 'PHALFEPXO' has elliptic apical lobes, oblong lateral lobes, leaf margins that are ruffled at the base, and flowers with a main color of yellow (RHS 7A), whereas 'PHALGLAZAL' has rhombic apical lobes, weakly spatulate lateral lobes, entire leaf margins, and flowers with a main color of light yellow (RHS 1D). Additionally, 'PHALFEPXO' has smaller flowers than 'PHALGLAZAL'.

I claim:

1. A new and distinct variety of *Phalaenopsis* plant named 'PHALFEPXPO', substantially as described and illustrated herein.

* * * * *